United States Patent [19]

Franz

[11] Patent Number: 4,505,736

[45] Date of Patent: Mar. 19, 1985

[54] N-PHOSPHONOMETHYLGLYCINE DERIVATIVES AND USE AS HERBICIDES

[75] Inventor: John E. Franz, Crestwood, Mo.

[73] Assignee: Monsanto Company, St. Louis, Mo.

[21] Appl. No.: 493,457

[22] Filed: May 11, 1983

[51] Int. Cl.³ .................. A01N 57/10; A01N 57/18; C07C 155/02
[52] U.S. Cl. ............................................ 71/76; 71/87; 260/455 P
[58] Field of Search ................ 260/455 P, 455 A; 71/76, 87

[56] References Cited

U.S. PATENT DOCUMENTS

| | | | |
|---|---|---|---|
| 3,991,095 | 11/1976 | Gaertner | 260/455 P |
| 4,035,177 | 7/1977 | Gaertner | 260/455 P |
| 4,211,732 | 7/1980 | Franz et al. | 260/455 P |
| 4,251,258 | 2/1981 | Kaufman | 260/455 P |

*Primary Examiner*—Henry R. Jiles
*Assistant Examiner*—Robert C. Whittenbaugh
*Attorney, Agent, or Firm*—David Bennett; Richard H. Shear; Arnold H. Cole

[57] ABSTRACT

N-alkoxythione derivatives of N-phosphonomethylglycine are novel compounds with utility as herbicides and in plant growth regulating applications.

9 Claims, No Drawings

N-PHOSPHONOMETHYLGLYCINE DERIVATIVES AND USE AS HERBICIDES

BACKGROUND OF THE INVENTION

This invention relates to a new class of organic chemical compounds. More particularly, it concerns novel derivatives of N-phosphonomethylglycine wherein a group, $R_1OC(S)$— (where $R_1$ has the significance indicated below), is attached to the nitrogen atom.

These compounds have plant regulating activity and can be used as plant growth regulators especially for sugarcane, as turf growth retardants, and at generally higher application levels, as herbicides.

DESCRIPTION OF THE INVENTION

The compounds of the invention have the formula:

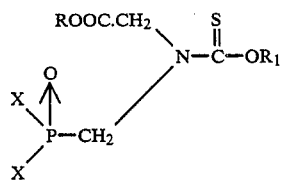

wherein R is selected from the group consisting of hydrogen and C to $C_6$ alkyl; $R_1$ is selected from $C_1$-$C_6$ alkyl, aryl, and $C_7$-$C_{10}$ aralkyl groups and each X is individually selected from the group consisting of hydroxyl and —OM wherein M is a salt-forming cation.

The preferred compositions of the invention are those in which at least one of the groups X is —OH. It is also preferred that the second group X is a group —$OM^1$ where $M^1$ is an agriculturally-acceptable salt-forming cation and particularly an alkali metal salt-forming cation such as sodium or potassium.

Although such cations are preferred, the salt can be formed by reaction of the acid with a nonmetallic cation. Compounds according to the invention, therefore, include the corresponding ammonium; organoammonium, (for example, trialkyl ammonium); organosulfonium, (for example, trialkyl sulfoxonium); and organophosphonium, (such as tetraalkylphosphonium) salts.

The group R can each be individually selected from substituted or unsubstituted $C_1$ to $C_6$ alkyl groups and this is understood to embrace both straight and branched-chain alkyl groups. The alkyl groups can therefore be, for example, methyl, ethyl, isopropyl, neopentyl, and n-hexyl. It is preferred, however, that R be a $C_1$ to $C_4$ alkyl group such as methyl, ethyl propyl, n-butyl, isopropyl, sec-butyl or tert-butyl. The groups are most preferably unsubstituted but they may bear substituents such as halogen (for example, a trifluoromethyl group), or a cyano or alkoxy group (as in a cyanomethyl or methoxy-ethyl group).

The group $R_1$ can be any of the R groups described above and can also be selected from aryl or $C_7$-$C_{10}$ aralkyl groups such as phenyl, benzyl or 2-phenylethyl.

The carboxylic and oxythione groups are either in the acid form or are esterified. In preferred compounds according to the invention, at least the oxythione group is in the esterified form, i.e., it is an alkoxythione.

U.S. Pat. No. 2,799,758 describes the production of N-phosphonomethylglycine (known as glyphosate) and certain of its derivatives, as well as the efficacy of such compounds as herbicides. Compounds of this general type are also described as effective plant growth regulators in U.S. Pat. No. 3,853,530. In addition, glyphosate derivatives in which the nitrogen atom is substituted by a O=C—SR group are described as herbicides in U.S. Pat. No. 3,911,095.

The invention also comprises agriculturally useful plant regulating compositions comprising use of an agriculturally-acceptable compound according to the invention in an amount effective to cause the desired species and degree of plant regulation and agricultural processes using such compositions.

The term "agriculturally-acceptable" as used herein is intended to restrict the application aspects of this invention to those compounds of the invention that can be applied to plants without leaving in the soil or in the plants themselves, where these are crops intended ultimately for human or animal consumption, unacceptable levels of residual material.

The term "plant regulation" as used herein includes both herbicidal effects and growth regulating effects. Thus, at higher application levels, the agriculturally useful compositions of the invention will have a herbicidal effect whereas at lower levels the effect will be of the growth regulating variety more fully described below.

The invention further comprises a process for the production of a composition according to the invention which comprises reacting a glyphosate derivative having the formula:

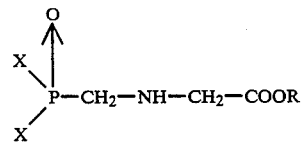

with an anhydrosulfide having the formula:

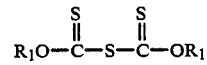

wherein X, $R_1$, and R have the significances indicated above, said reaction being carried out in an aqueous reaction medium with a pH of at least 8.

The reaction is conveniently carried out at around or below room temperature in a water/alcohol solvent mixture or any other solvent or solvent mixture in which the reactants can be dissolved and effectively reacted.

DESCRIPTION OF PREFERRED EMBODIMENTS

EXAMPLE 1

This Example describes a process for the production of a compound of the invention having the formula:

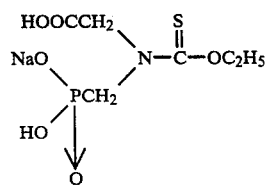

A solution of 0.85 g. (0.005 mole) of glyphosate (N-phosphonomethylglycine) and 0.40 g. (0.010 mole) of sodium hydroxide in 10 ml. of water and 10 ml. of ethanol was prepared. To this solution was added 1.2 g. (0.0057 mole) of an anhydrosulfide having the formula:

followed by 4.6 of a 10% w/v solution of sodium hydroxide. Addition of the sodium hydroxide was performed incrementally to mantain the pH at 8 and was accompanied with stirring and shaking.

The final mixture was a yellow solution containing a small amount of flocculated solid. After cooling to room temperature for an hour, the mixture was filtered. Analysis of the residue indicated that it was unreacted thio anhydride starting material.

The filtrate was extracted using petrol/ether, partially concentrated at reduced pressure to remove ethanol; and then acidified to pH 2 using hydrochloric acid. Carbon disulfide, formed during acidification, was evacuated using a water vacuum and the clear solution that remained was concentrated at a pressure of 0.5 mm of mercury. The residue was twice extracted with about 30 ml. portions of ethanol and finally washed with ether and air-dried. What remained was 1.9 g. of a white powder, the infra-red spectrum and elemental analysis of which were consistent with the formula given above. The product was extracted several times with methanol until the infra-red spectrum of the remainder indicated only sodium chloride. The methanol extractants were combined and diluted with ethyl acetate and stored at room temperature. A white residue formed and after the supernatant liquid had been decanted, the residue was diluted with ethyl acetate and centrifuged. The residue (0.7 g.) was washed with ether and air-dried. The infra-red spectrum was consistent with the expected structure. The melting point of the solid was 212° C. (with decomposition). Upon resolidification a second melting point (with decomposition) at 325° C. was observed.

Analysis of the product showed the following elemental analysis: C—25.82%, H—4.05%, N—4.95%.

The theoretical proportions for the expected structure are: C—25.81%, H—3.98%, N—5.02%.

EXAMPLE 2

This example describes a process for the production of a compound of the invention having the formula:

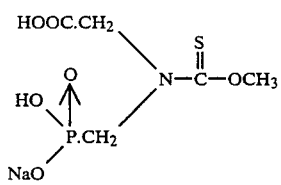

A suspension of 2.0 g. (0.012 mole) of glyphosate (N-phosphonomethylglycine) in 40 ml. of deionized water was prepared and found to have a pH of 2.5.

To this suspension were added 2.4 g. (0.013 mole) of carbonodithioic acid anhydrosulfide dimethyl ether, 50 ml. of ethanol and then, over a five minute period, 10 ml. of a 10% solution of sodium hydroxide after which the pH reached 8.3. The pH was kept at about this level by occasional additions of sodium hydroxide solution as needed. After about three hours the pH has stabilized at 8.5 after a total of 17.3 ml. of the sodium hydroxide had been added and the solution had a clear yellow color. This solution was then washed with petrol/ether (50 ml.) and the ethanol was removed under vacuum. The remaining aqueous solution was acidified to pH 2.0 with concentrated hydrochloric acid, causing the solution to become cloudy. The solvent was removed on a rotovaporizer leaving 4.65 g. of a white solid. This solid was extracted four times using methanol. (Ethyl acetate was added to the extract in an amount that was allowed to stand overnight.) A white precipitate (1.0 g.) formed and was isolated by centrifugation. On standing, a further half gram of precipitate separated from the decanted methanol/ethyl acetate solution.

Both precipitates were taken up in 30 ml. of methanol and a slight amount (0.07 g.) of precipitate was removed by centrifugation.

After removal of the methanol, 0.8 g. of a white solid remained. Proton NMR analysis of the residue indicated that it contained about 0.37 mole of methanol. The elemental anlaysis for the carbon, hydrogen, and nitrogen calculated for $C_5H_9O_6P_1S_1Na$, with 0.37 mole of methanol and 0.55 mole of water is: C—22.47%, H—4.06%, N—4,88%.

The values actually found were: C—22.10%, H—3.75%, N—4.67%.

EXAMPLE 3

Using essentially the same technique described in Example 2, the corresponding n-butyl ester was produced. The reaction was run using 2 g. of glyphosate reacted with a molar equivalent of carbonodithioic acid anhydrosulfide, di-n-butyl ether. A total of 16 ml. of 10% sodium hydroxide was added during the reaction. The mixture was stirred for about 24 hours and then the petrol/ether extraction was prepared before acidification with concentrated hydrochloric acid to pH 3.

After solvent removal, methanol extraction, ethyl acetate addition and collection and drying of the resulting precipitate, the 1.9 g. of product was analyzed.

The target formula:

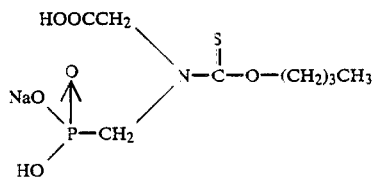

requires an analysis of: C—31.27%, H—4.92%, N—4.59%.

The actual analysis yielded: C—31.14%, H—4.92%, N—4.59%.

The melting point of the product was 188° C. (with decomposition).

EXAMPLE 4

A solution of 2.5 g. of glyphosate in 30 ml. of deionized water was mixed with a solution of 3.7 g. of carbonodithioic acid anhydrosulfide di-n-propyl ether. The mixture was stirred vigorously using a magnetic stir bar. The pH of the mixture, initially about 3.1, was adjusted to 9.5 by the slow addition of 12.0 ml. of 10% sodium hydroxide and maintained at from 9.0 to 9.5 by occasional additions of sodium hydroxide. The mixture was stirred overnight and next day was washed three times with petrol/ether. The washed aqueous/alcoholic layer was placed in a rotovaporizer to remove most of the ethanol. The pH of the aqueous residue was adjusted to about 3.0 using concentrated hydrochloric acid and a precipitate began to form. After being allowed to stand overnight, 1.3 g. of precipitate with a melting point of 198° C. (with decomposition) was removed by filtration.

The target compound has a formula:

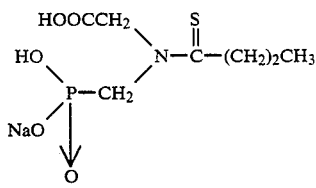

and, with a calculated 0.8 mole of water, the expected elemental analysis is: C—27.38%, H—4.78%, N—4.55%.

The actual analysis of the precipitate showed: C—27.32%, H—4.38%, N—4.38%.

EXAMPLE 5

This Example describes the production of a compound having the formula:

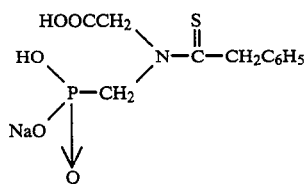

In a solvent mixture of 30 ml. of deionized water and 40 ml. of ethanol were dissolved 2.0 g. of glyphosate (0.012 mole) and 4.3 g. of carbonodithioic acid anhydrosulfide, dibenzyl ether. The reaction mixture was stirred vigorously and was found to have a pH of 3.2. A slow addition of 10% sodium hydroxide was initiated and continued until the pH had reached 9.5. The pH was maintained between 9 and 10 by occasional additions of the same sodium hydroxide over a period of two days after which a total of 13.8 ml. had been added.

The solution was washed three times with petrol/ether and the aqueous/alcoholic layer was placed in a rotovaporizer until about half the volume had been removed. The pH of the remainder was then adjusted to 2.8 using concentrated hydrochloric acid. The solution became cloudy and the solvent was removed in vacuo to leave a resinous solid.

This residue was extracted several times with methanol and the extract was combined and mixed with ethyl acetate until the solution became cloudy. After being allowed to stand overnight, 0.4 g. of a white precipitate was removed by filtration. The precipitate had a melting point (with decomposition) of 195° C.

The comparison of calculated with measured elemental contents is as follows:

|   | Calculated | Found |
|---|---|---|
| C | 38.71% | 37.97% |

| | Calculated | Found |
|---|---|---|
| H | 3.84% | 3.60% |
| N | 4.10% | 4.08% |

EXAMPLE 6

A solution was prepared comprising 2.5 g. of glyphosate (0.015 mole) and 3.7 g. of carbonodithioic acid anhydrosulfide, diisopropyl ether (0.016 mole) dissolved in an agitated mixture of 10 ml. of deionized water and 20 ml. of ethanol. The pH of the solution was found to be 3.2 and this was then adjusted to 9.5 by the addition of about 15 ml. of 10% sodium hydroxide. The pH was maintained between 9 and 10 by addition of more of the same sodium hydroxide to the agitated solution over the next 72 hours.

The solution was then filtered to remove undissolved material and the filtrate was twice washed using petrol/ether, reduced to half volume using a rotovaporizer and acidifed to pH 3 using concentrated hydrochloric acid. This produced a cloudy solution from which 4.5 g. of a dry white solid were recovered on removal of the solvent. This solid was placed in a soxhlet extractor and extracted with methanol overnight. A white solid material (1.4 g. melting point 196° C. with decomposition) was separated by filtration.

The product was a mixture of the monosodium and disodium salts of:

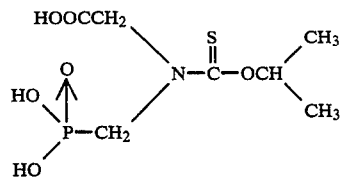

For such a mixture, the calculated and measured percentages of carbon, hydrogen, and nitrogen are as follows:

|   | Expected* | Found |
|---|---|---|
| C | 26.84% | 26.75% |
| H | 4.34% | 4.30% |
| N | 4.47% | 4.40% |

*For a $C_{14}H_{25}N_2O_{12}S_2P_2Na_3 \cdot H_2O$ composition (i.e., a 1:1 molar mixture)

EXAMPLE 7

A solution of 2.0 g. of ethyl glyphosate (0.01 mole) and 2.3 g. of carbonodithioic acid anhydrosulfide, diethyl ether, (0.011 mole) in 10 ml. of deionized water and 20 ml. of ethanol was agitated while the pH was adjusted from 3.0 to 9.0 by slow addition of 8.2 ml. of 10% sodium hydroxide. Over time, the pH was maintained at about 8.5 by further additions of sodium hydroxide. After 1½ hours, a total of 17.4 ml. had been added. Unreacted anhydrosulfide was removed by filtration and the filtrate was thrice washed with petrol/ether.

The filtrate was then distilled in vacuo to half volume to remove much of the ethanol from the solution and the aqueous residue was acidified to pH 2.5 using concentrated hydrochloric acid. The remainder of the solvent was then removed and the gummy residue dried by azeotroping with toluene. After stripping the toluene, 4.0 g. of a white solid remained and this was thoroughly extracted using methanol. The methanol extracts were combined and stripped to a volume of 3.0 ml. and insoluble residue removed by centrifugation.

The liquid layer was then treated with approximately 200 ml. of acetonitrile yielding a flocculant precipitate. The mixture was allowed to stand overnight before being filtered. The filtrate yielded 1.5 g. of white solid when the solvent was stripped off. This was the sodium salt of the desired derivative. The acid form was generated by treatment of its aqueous solution with an ion exchange resin (Amberlite IR-120 plus). The water was then removed in vacuo and the residue was extracted with ethyl acetate. Petrol/ether was added to the solution to precipitate an oil, which when heated to 70° C. at 1.0 mm of mercury to remove solvent traces yielded the desired acid form.

The formula:

$$\begin{array}{c}C_2H_5OOCCH_2\\ \diagdown \\ HO\diagdown \overset{O}{\underset{\diagup}{\uparrow}} N-\overset{S}{\underset{\|}{C}}-OC_2H_5 \\ P-CH_2 \\ HO\diagup \end{array}$$

should show an elemental analysis of: C—31.68%, H—5.98%, N—4.61%.

In fact, analysis showed: C—31.80%, H—5.65%, N—4.82%.

EXAMPLE 8

This example illustrates the post-emergence herbicidal activity of the compounds produced in Examples 1 and 5, designated A and B respectively.

In each case, the compound (A or B) was applied in spray form to 14 day old specimens of the various plant species indicated in Table 1 (below).

The additive was incorporated in a spray solution comprising 3 parts of cyclohexanone and 1 part of a surfactant (35 parts of the butylamine salt of dodecylbenzenesulfonic acid and 65 parts of tall oil condensed with ethylene oxide in the ratio of 11 moles of ethylene oxide to 1 mole of tall oil).

The application rate of the spray was varied as indicated and the treated plants were placed in a greenhouse in good growing conditions. After the indicated period, the effect on the plants was examined and rated according to the following index:
0 indicates less than 25% of the plants are injured
1 indicates 25 to 49% injured
2 indicates 50 to 74% injured
3 indicates 75 to 99% injured
4 indicates all plants killed

TABLE I

| Plant Species | Additive A (Ex. 1) Appl. Rate 5.6 kg/ha | | Additive B (Ex. 5) Appl. Rate 5.6 kg/ha | |
|---|---|---|---|---|
| | 2 WAT | 4 WAT | 2 WAT | 4 WAT |
| Soybean | 1 | 1 | 1 | 1 |
| Sugar Beet | 3 | 4 | 3 | 4 |
| Wheat | 1 | 3 | 1 | 1 |
| Rice | 1 | 2 | 0 | 1 |
| Sorghum | 1 | 2 | 1 | 2 |

TABLE I-continued

| Plant Species | Additive A (Ex. 1) Appl. Rate 5.6 kg/ha | | Additive B (Ex. 5) Appl. Rate 5.6 kg/ha | |
|---|---|---|---|---|
| | 2 WAT | 4 WAT | 2 WAT | 4 WAT |
| Cocklebur | 2 | 1 | 2 | 2 |
| Wild Buckwheat | 2 | 2 | 2 | 2 |
| Morningglory | N | N | 2 | 2 |
| Hemp Sesbania | 1 | 1 | 1 | 3 |
| Common Lambsquarters | 3 | 4 | 4 | 4 |
| Pa. Smartweed | 3 | 3 | 4 | 4 |
| Velvetleaf | 1 | 2 | 1 | 2 |
| Downy Brome | 1 | 1 | 2 | 2 |
| Proso Millet | 3 | 4 | 2 | 2 |
| Barnyardgrass | 2 | 3 | 1 | 2 |
| Large Crabgrass | 3 | 3 | 3 | 2 |

Note:
N indicates "Not Tested"
WAT indicates "Weeks after Treatment"

EXAMPLE 9

The following example illustrates the use of the compounds of the invention as plant growth regulants and, specifically, as retardant for the growth of grasses.

The indicated compounds were made up into aqueous solutions containing a surfactant.

The solutions were then applied to grass plants that were approximately 14 days old at the indicated rate. After two weeks, the length of grass plants was measured and compared with the length of a control plot that had been sprayed with a solution identical to that described, save that the compound of the invention was omitted. The length was expressed as a percentage of that of the control plot grass.

At the same time, the phytotoxicity of the treatment solution was assessed and noted using the scale set forth in Example 8. The data obtained, which comprises data from several replicated experiments, is given in Table II below.

TABLE II

| Additive From: | Application Rate (kg/ha) | Mean Grass Height (mm) | Percent of Control Grass Height |
|---|---|---|---|
| Example 3 | 0.56 | 117.5 | 83.4 |
| | 2.24 | 77.5 | 55.0 |
| | 5.60 | 47.5 | 33.7 |
| | 5.60 | 50.0 | 44.2 |
| Example 4 | 0.56 | 97.5 | 69.2 |
| | 2.24 | 65.0 | 46.2 |
| | 5.60 | 50.0 | 35.5 |
| | 5.60 | 43.5 | 34.1 |
| Example 5 | 0.56 | 37.5 | 32.0 |
| | 2.24 | 22.5 | 19.2 |
| | 5.60 | 23.5 | 20.0 |
| | 5.60 | 27.5 | 22.9 |
| | 5.60 | 38.5 | 69.4* |

*This result is apparently an aberration, as it is quite inconsistent with other results (see table) at the same application level.

From the above data, it will be apparent that the additives of the invention are very effective inhibitors of grass growth.

EXAMPLE 10

This example shows the effectiveness of compounds of the invention in increasing the sucrose content of sugarcane.

In determining the effects of the compound of this invention on sugarcane, it should be noted that the appropriate rate of application can vary from about 0.122 kg/hectare to about 5.6 kg/hectare. Depending upon local cultural practices in various areas around the world, sugarcane is grown from about 9 to 30 months before harvest, and it is thus necessary to consider both the chronological age and the maturity stage of the cane in rate determinations. Application of the treatment to the case is generally made from about 2 to 12 weeks prior to the scheduled harvest date. Preferably, such applications are made from 3 to 10 weeks before said date.

In this test, individual sugarcane stalks are treated with compounds of this invention from 4 to 6 weeks before harvest. To avoid sampling errors, 18-month old cane is employed in the tests. For each compound employed, at least five stalks are used, processed, and the total values obtained are averaged for each stalk. An identical number of untreated sugarcane stalks of the same age are similarly processed to provide a control. A comparison of the values obtained for the treated cane with the control sample provides a convenient means of determining the effectiveness of these compounds.

The analyses are carried out using Test No. 80R-73 (12.11.80) developed by the Hawaiian Sugar Planters Association. The results are expressed as Juice Purity and Pol percent Cane. Pol percent Cane is a polarimetric determination and equals the percentage of sucrose if it is the only substance in the solution which will rotate the plane of polarized light. A determination of Pol percent Cane is considered by those skilled in the art as an effective means of determining the sucrose content of sugarcane juice.

In order to convert a change in Pol percent Cane into a corresponding change in the quantity of sugar obtained, it is first necessary to know the average normal yield of sugar in the area under test. Here, the tests are carried out in a region where about 225 to 245 metric tons of cane are harvested per hectare.

The indicated amount of the additive is dissolved in about 0.3 ml. of water. To this solution there is added a small amount (about 0.1% of the final volume) of a commercial nonionic surfactant (nonylphenol ethoxylated to contain about 9.5 mols of ethylene oxide per mol of nonylphenol). Such a solution is then applied to the whorl of each of the stalks to be tested with the exception of the control stalks. At the time of application, internode number 13 on each stalk is marked as a reference point. At 4 and 5 weeks (as indicated) after treatment (WAT), the plants are harvested and the portion from the reference point to the shoot apex of each stalk of a treated or untreated group is removed, combined and analyzed as described. The results obtained are as described in Table III.

TABLE III

| Compound | Application Level (mg. per stalk treated) | 4 WAT PPC* | 4 WAT Purity | 5 WAT PPC* | 5 WAT Purity |
|---|---|---|---|---|---|
| Example 1 | 30 | 9.55 | 74.99 | 10.64 | 79.05 |
| Control | — | 7.50 | 70.26 | 8.48 | 73.95 |
| Example 3 | 38 | 9.67 | 78.08 | 10.39 | 78.81 |
| Control | — | 8.10 | 71.80 | 7.62 | 71.08 |
| Example 4 | 38 | 7.19 | 67.87 | 12.34 | 85.40 |
| Control | — | 8.10 | 71.80 | 7.62 | 71.80 |

*POL percent cane

As has been demonstrated above, the compounds of the invention have significant herbicidal activity and are also useful as plant growth regulators; for example, for application to sugarcane to enhance sucrose deposition and as turf growth retardants.

A plant growth regulator is a chemical substance that alters the natural growth or development of a plant to enhance various agricultural or horticultural features. As employed herein, the term "natural growth or development" designates the normal life cycle of the plant in accordance with its genetics and its environment, in the absence of artificial, external influences.

It is to be understood that the regulation of natural growth and development does not include killing or herbicidal action. Although phytotoxic or lethal amounts of the active ingredient can be employed to destroy plants, growth regulating effects require only such nonlethal amounts of said active ingredient as will serve to regulate the natural growth and development of useful plants without substantial injury. As may be expected and as long understood by those skilled in the art, such effective plant regulating amounts will vary, not only with the particular active ingredient selected for treatment, but also with the regulatory effect to be achieved, the species of plant being treated and its stage of development, and whether a permanent or transient regulating effect is sought. Other factors which may bear upon the determination of an appropriate plant regulating amount include the plant growth medium, the manner in which the treatment is to be applied, weather conditions such as temperature or rainfall, and the like.

It has been found that desirable regulation of natural plant growth or development is achieved by application of the compounds of the invention to plants in various stages of development. Accordingly, the compounds can be applied directly to the plant in seedling stage, flowering stage or fruiting stage and the like or can be applied sequentially to plants at more than one stage of development. Such application may be made directly to one or more of the plant's parts, such as stems, leaves, flowers, fruit or the like. Genrally, the application is made by spraying the plants using conventional techniques.

Regulation of the natural growth or development of plants by chemical treatment results form the effect of the chemical substance on the physiological processes of the plant and the effect of such substance may be manifested by the morphology of the plant. As should be readily apparent, said regulation may also result from a combined or sequential effect of the chemical manifesting a response in both physiology and morphology.

In general, regulation of the natural growth or development which leads to a morphological change in the plant is readily noticeable by visual observation. Such changes can be found in the size, shape, color, or texture of the treated plant or any of its parts. Similarly, changes in the quantity of plant fruit or flowers can be simply noted.

On the other hand, regulation which leads to changes only in the physiological processes occur within the treated plant and are usually hidden from the eye of an observer. Changes of this type are most often in the production, location, storage, or use of naturally occurring chemicals, including harmones, within the plant. Physiological changes in a plant often are recognized when followed by a subsequent change in morphology. Additionally, there are numerous analytical procedures known to those skilled in the art for determining the nature and magnitude of changes in the various physiological processes.

It is desirable to use in the compositions of the invention, in addition to an effective amount of the active ingredient, an adjuvant to facilitate a uniform distribution of the compound of the plants. Adjuvant, as used herein, includes one or more materials in liquid or solid form. Thus, suitable adjuvants are diluents, extenders, carriers, surfactants, foaming agents, solvents and, usually, combinations thereof. The compositions can be in numerous forms, such as dusts, powders, water soluble powders, wettable powders, solutions, foams, dispersions, or emulsions. Generally, it is preferred to use one or more surfactants in the compositions which aid in wetting the treated plant surface and for providing stable dispersions of the active ingredient in various inert carriers or diluents in the composition or added to the composition prior to application to the plants. Suitable surfactants which can be employed in the compositions of this invention are well known surface active agents, such as wetting agents, emulsifiers, dispersing agents, and can be nonionic, anionic, or cationic. Preferred surfactants are the nonionic or the anionic type which are widely used in compositions employed in agronomic treatments. Representative nonionic surfactants are polyoxyethylene esters of fatty acids, octylphenyl polyethylene glycol ethers, polyoxyethylene derivatives of long-chain alcohols, and the like. Representative anionic surfactants are alkali and alkaline earth salts of alkylarylsulfonic acids such as sodium lauryl sulfonate, dialkyl sodium sulfosuccinate esters, and the like. Such surfactants are well known and reference is made to U.S. Pat. No. 2,547,724 for detailed examples of same.

Usually, the compositions of this invention take the form of a concentrate which can be readily extended with an inert carrier prior to application to the plants. Said concentrates in liquid form generally consist of a solvent, surfactant, emulsifier, defoamer and/or other additive and about 25 to 75 percent by weight of the active ingredient. These liquid concentrates can be diluted with water to provide a composition suitable for application to plants which contains from about 0.1 to about 15 percent, and commonly from about 1.0 to 10 percent by weight of the active ingredient. Concentrates in solid form are, for example, water soluble powders consisting of finely divided solids such as calcium silicate, surfactant and from about 5 to 80 percent or more by weight of the active ingredient which are diluted with water prior to applying to the plants. Broadly, the compositions herein may contain from 0.1 to 80 percent or more by weight of the active ingredient. These compositions may be applied at rates of from 0.06 to 22.4 kg/ha or more, a preferred range being from 1.12 to 11.2 kg/ha, as more particularly detailed below.

In selecting the appropriate rate of application of the active ingredient, it will be recognized that precise dosages will be dependent upon the plant species being treated, the particular plant part or habitat to which application is made, the development stage of the plant, the particular chemical employed, the mode of application and various other factors known to those skilled in the art. In foliar treatment for the regulation of plant growth, the active ingredients are applied in amounts from about 0.058 to about 11.2 or more kilograms per hectacre. Foliar applications of from 0.112 to 7 kilograms of the active ingredient per hectacre are preferred. In applications to the soil habitat of the plants the active ingredients are applied to the soil at a rate of from 0.112 to 11.2 kilograms per hectacre, and in particular embodiments at rates of from 1.12 to 7 kg/ha. Foliar application to plants at the blooming stage, e.g., 10 percent blossoms, are preferred. For herbicidal effects, the application rate will more frequently be in the range of 2.4 to 11.2 kg/ha per kg/ha and application is made by preference to the plant itself.

What is claimed is:

1. A compound having the formula:

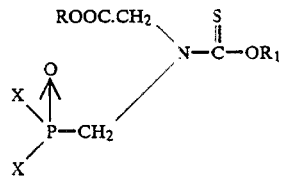

wherein R is selected from the group consisting of hydrogen and $C_1$ to $C_6$ alkyl groups; $R_1$ is selected from $C_1$ to $C_6$ alkyl, phenyl and $C_6$-$C_{10}$ aralkyl groups; and the Xs can be identical or different and are individually selected from the group consisting of hydroxyl and —OM wherein M is a salt-forming cation.

2. A compound according to claim 1 in which at least one group X is a hydroxyl group.

3. A compound according to claim 1 in which the group R is hydrogen.

4. A compound according to claim 1 having the formula:

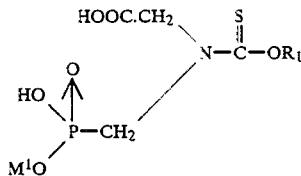

where $M^1$ is an alkali metal and $R_1$ is a $C_1$ to $C_6$ alkyl group.

5. A herbicidal method which comprises application to a plant of a herbicidally-effective amount of an agriculturally-acceptable compound according to claim 1.

6. A herbicidal method which comprises application to a plant of a herbicidally-effective amount of an agriculturally-acceptable compound according to claim 4.

7. A plant growth regulating method which comprises applying a growth regulating amount of an agriculturally-acceptable compound according to claim 1.

8. A plant growth regulating method which comprises applying a growth regulating amount of an agriculturally-acceptable compound according to claim 4.

9. A process for the production of a compound according to claim 1 which comprises reacting a glyphosate derivative having the formula:

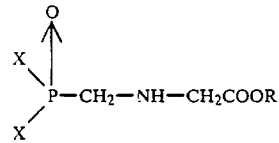

with an anhydrosulfide having the formula:
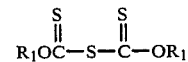
wherein X, $R_1$ and R have the significances set forth in claim 1, said reaction being carried out in an aqueous reaction medium with a pH of at least 8.
* * * * *